United States Patent [19]

Miller et al.

[11] Patent Number: 5,300,057
[45] Date of Patent: Apr. 5, 1994

[54] FRONTAL TAPE-BASED DIAPER CLOSURE SYSTEM

[75] Inventors: John A. Miller, Woodbury, Minn.; Earl Tate, Jr., Bedford Park, Ill.; Ruben E. Velasquez Urey, St. Paul, Minn.; Yasuhiro Kono; Yoshihiro Akiyama, both of Tokyo, Japan; Robert S. Mulder, Shoreview, Minn.

[73] Assignee: Minnesota Mining and Manufacturing Company, St. Paul, Minn.

[21] Appl. No.: 950,204

[22] Filed: Sep. 24, 1992

Related U.S. Application Data

[63] Continuation-in-part of Ser. No. 808,044, Dec. 12, 1991, abandoned, which is a continuation of Ser. No. 616,226, Nov. 20, 1990, abandoned.

[51] Int. Cl.⁵ ............................................. A61F 13/15
[52] U.S. Cl. ..................................... 604/390; 604/389
[58] Field of Search ........................... 604/389–391; 525/97, 98; 428/355

[56] References Cited

U.S. PATENT DOCUMENTS

| | | | |
|---|---|---|---|
| 2,532,011 | 11/1950 | Dahlquist et al. | 154/53.5 |
| 3,239,478 | 3/1966 | Harlan, Jr. | 260/27 |
| 3,427,269 | 2/1969 | Davis et al. | 260/27 |
| 3,932,328 | 1/1976 | Korpman | 260/27 BB |
| 3,935,338 | 1/1976 | Robertson | 427/207 |
| 3,954,692 | 5/1976 | Downey | 260/33.6 AQ |
| 4,080,348 | 3/1978 | Korpman | 260/27 BB |
| 4,097,434 | 6/1978 | Coker, Jr. | 260/23.3 |
| 4,136,071 | 1/1979 | Korpman | 260/27 BB |
| 4,388,349 | 6/1983 | Korpman et al. | 427/208.4 |
| 4,460,364 | 7/1984 | Chen et al. | 604/387 |
| 4,540,415 | 9/1985 | Korpman | 604/390 |
| 4,554,191 | 11/1985 | Korpman | 428/35 |
| 4,719,261 | 1/1988 | Bunnelle et al. | 525/97 |
| 4,729,971 | 2/1988 | Pape et al. | 428/40 |
| 4,731,066 | 3/1988 | Korpman | 604/366 |
| 4,778,701 | 10/1988 | Pape et al. | 428/40 |
| 4,780,367 | 10/1988 | Lau et al. | 428/355 |
| 4,801,480 | 1/1989 | Panza et al. | 428/40 |
| 4,813,947 | 3/1989 | Korpman | 604/387 |
| 5,019,071 | 5/1991 | Bany et al. | 604/389 |
| 5,024,672 | 6/1991 | Widlund | 604/390 |
| 5,028,646 | 7/1991 | Miller et al. | 524/77 |

FOREIGN PATENT DOCUMENTS

| | | | |
|---|---|---|---|
| 0249461 | 12/1987 | European Pat. Off. | A61L 15/06 |
| 0306232 | 3/1989 | European Pat. Off. | C09J 3/14 |

Primary Examiner—Randall L. Green
Assistant Examiner—Rob Clarke
Attorney, Agent, or Firm—Gary L. Griswold; Walter N. Kirn; William J. Bond

[57] ABSTRACT

A tape closure system exhibiting high shear and high non-shocky peel to a low adhesion backsize coated substrate is disclosed. The adhesive used on the fastening tape used in the closure system comprises a high diblock ($\geq 25$ percent) styrene-isoprene-styrene elastomer component with a composite midblock glass transition temperature of 244 to 264 Kelvin with 30 to 60 percent elastomer.

15 Claims, 2 Drawing Sheets

FIG.1

FRONTAL TAPE-BASED DIAPER CLOSURE SYSTEM

BACKGROUND AND FIELD OF THE INVENTION

This application is a continuation-in-part of U.S. Ser. No. 07/808,044, filed Dec. 12, 1991, now abandoned; a continuation of U.S. Ser. No. 07/616,226, filed Nov. 20, 1990, now abandoned.

This invention relates to an improved pressure-sensitive adhesive for use with adhesive diaper closure tapes and the like, and more specifically, to a pressure-sensitive adhesive composition which provides improved performance characteristics when used in a diaper closure system having an adhesion surface treated with a release agent.

There are numerous patents and literature documents that are directed to the use of block copolymers in adhesive compositions which traditionally include a block copolymer such as an A-B-A block copolymer and a tackifying resin. U.S. Pat. No. 3,427,269 (Davis), describes the use of an elastomeric based adhesive comprising at least 100 parts of an A-B-A block copolymer, a rosin ester (10-50 parts) and a coumarone-indene resin (25-50 parts). However, as development of these elastomer based compositions has progressed it has been found that the adhesive properties of these block copolymer based adhesive compositions are extremely sensitive to the particular block copolymer(s) used, and the proportion and type of modifiers such as solid or liquid tackifiers, aromatic or aliphatic tackifiers, plasticizers, extender oils, curing agents and the like.

U.S. Pat. No. 3,932,328 (Korpman) describes the use of a prior art adhesive based on an A-B-A block copolymer with a solid tackifying resin and an extender oil. He describes this composition as unsatisfactory as a pressure-sensitive adhesive(PSA) and proposes a specific composition comprising a styrene-isoprene-styrene (SIS) copolymer and specific proportions of an aliphatic solid tackifier and a liquid tackifier (at 25° C.). Korpman reports that his adhesive had "satisfactory" adhesion and quick-stick for most applications. The prior art patent Korpman was referring to was U.S. Pat. No. 3,239,478 (Harlan) who discloses both PSA and non-PSA A-B-A block copolymer based adhesives. Harlan only exemplifies a PSA formed of 100 parts of a SIS block copolymer (48 percent S), 75 parts of a 2% aromatic extender oil and 125 parts of a tackifying resin of glycerol ester of polymerized rosin.

U.S. Pat. No. 3,954,692 (Downey) also addressed the problems with A-B-A based adhesive compositions, particularly hot melt pressure-sensitive adhesive compositions, particularly problems with providing adequate adhesion and strength properties. Downey et al. was particularly concerned with providing a general-use, pressure-sensitive adhesive with not only adequate tack but good peel strength and good shear strength. Downey et al. proposed an SIS block copolymer admixed with conventional extender oils, which were stated as unsatisfactory by Korpman, using a specific tackifying resin. The resin exemplified comprised a polymerized admixture of piperylene and 2-methyl-2-butene, which is currently marketed, e.g., as Wingtack TM 95, available from Goodyear Chemical Company.

An alleged improvement, for an adhesive designed to be used with porous substrates (e.g., Kraft paper), on the Downey et al. formulation is proposed by U.S. Pat. No. 4,097,434 (Coker) which describes conventional practice as using extending oils with low aromatic content in formulations in which extending oils are employed. Coker states that these formulations have inadequate holding power to porous substrates and proposes a formulation of an A-B-A copolymer (only SIS is exemplified) with a tackifying resin (only the Downey et al. Wingtack TM 95 is exemplified) and an extending oil with a high aromatic content (above 55%) and a saturates content of less than 15%. The two oils compared were Shellflex TM 371 (non-invention) and Dutrex TM 739 (as per the claimed invention). The Shellflex TM 371 formulations were nominally presented to show formulations with inadequate adhesion properties.

Another variation is proposed in U.S. Pat. No. 4,460,364 (Chen et al.) which describes a composition having certain rheological properties that they propose are indicative of A-B-A based adhesives with tenacious bonding and clean release, where the B block is a polyolefin (only polystyrene-polyethylene polybutylene-polystyrene exemplified). The SEBS copolymers exemplified are used with a solid tackifying resin and a plasticizing or extending oil. Chen et al. states that these compositions do not sacrifice clean release for tenacity as is stated is typically done in prior art hot melt PSAS. Chen et al. was primarily concerned with an adhesive which could be used in a sanitary napkin without leaving residue adhesive on the undergarment. This rheological approach is also proposed by U.S. Pat. No. 4,719,261 (Bunnelle et al.) who uses the same rheological properties to define a hot melt PSA that allegedly can also be used as an elastic. The specific compositions claimed comprise specific A-B-A (i.e., SIS) copolymers (45-75%) with both aromatic (2-9%) and aliphatic (25-50%) solid resins.

U.S. Pat. No. 3,935,338 (Robertson et al.) describes an adhesive composition that allegedly has a low enough viscosity to be applied as a hot melt and will have enhanced PSA properties at elevated temperatures. The formulation exemplified as meeting this requirement is an SIS block copolymer (100 parts) with an elastomer block compatible resin (50-200 parts), a reinforcing resin (25-100 parts) and an extending oil (25-100 parts). The patent also discloses compositions excluding the reinforcing resin as counterexample formulations that have inadequate adhesive properties at elevated temperatures.

Korpman has also proposed modifications to his formulations, and approach; U.S. Pat. No. 4,813,947 (use of a A-B-A(SIS) and a tackifier which is coupled with a specific hot melt landing area); 4,540,415 (use of a SIS a solid tackifier and a phosphatide) and 4,080,348 and 4,136,071 (addition of an SI block copolymer).

Although there exists extensive art on the use of block copolymers in PSA compositions, due to the uncertainty in results and continuing need, the search continues for adhesive formulations with yet improved mixes of properties such as adhesion characteristics, such as shear strength and peel strength. Particularly, there is the continuing need for the identification of adhesive formulations that have a proper mix of adhesive properties such as would make them particularly suitable for use in diaper closure systems. The engineering of diapers is highly specialized. Adhesive closure systems used in this environment ideally should have a particular set of properties.

SUMMARY OF THE INVENTION

It has been found that a hot melt coatable pressure-sensitive adhesive can be provided which has advantageous adhesion and cohesive properties when used on a fastening tab in a diaper closure system having a release treated adhesion surface which adhesive composition comprises:

(a) 30 to 60 weight percent of an elastomeric A-B (A) block copolymer of at least one polystyrene block A and at least one polyisoprene block B, wherein the A blocks comprise from 10% to 30% of the copolymer and at least 25 percent of said A-B block copolymer comprises an A-B diblock copolymer with the balance comprising an A-B-A block copolymer, and (b) a mixture of solid tackifying resin, liquid tackifying resin and/or plasticizing oil so as to provide a composite midblock glass transition temperature of from about 264 to 244 Kelvin, which adhesive composition exhibits a non-shocky peel and a 135° peel strength of greater than approximately 300 grams per inch (as defined herein) to release coated substrate, and a shear strength of at least 100 minutes (as defined herein) to the same substrate.

This composition is described in a cartesian space system where the CMTg values are on the x-axis and the percent elastomer is on the y-axis.

Below an adhesive midblock glass transition temperature of 244 Kelvin, there is provided an adhesive having a non-shocky peel and a 135° peel strength of generally greater than approximately 200 grams per inch, preferably greater than 250 grams per inch.

DETAILED DESCRIPTION OF THE PREFERRED EMBODIMENTS

Figure 1:
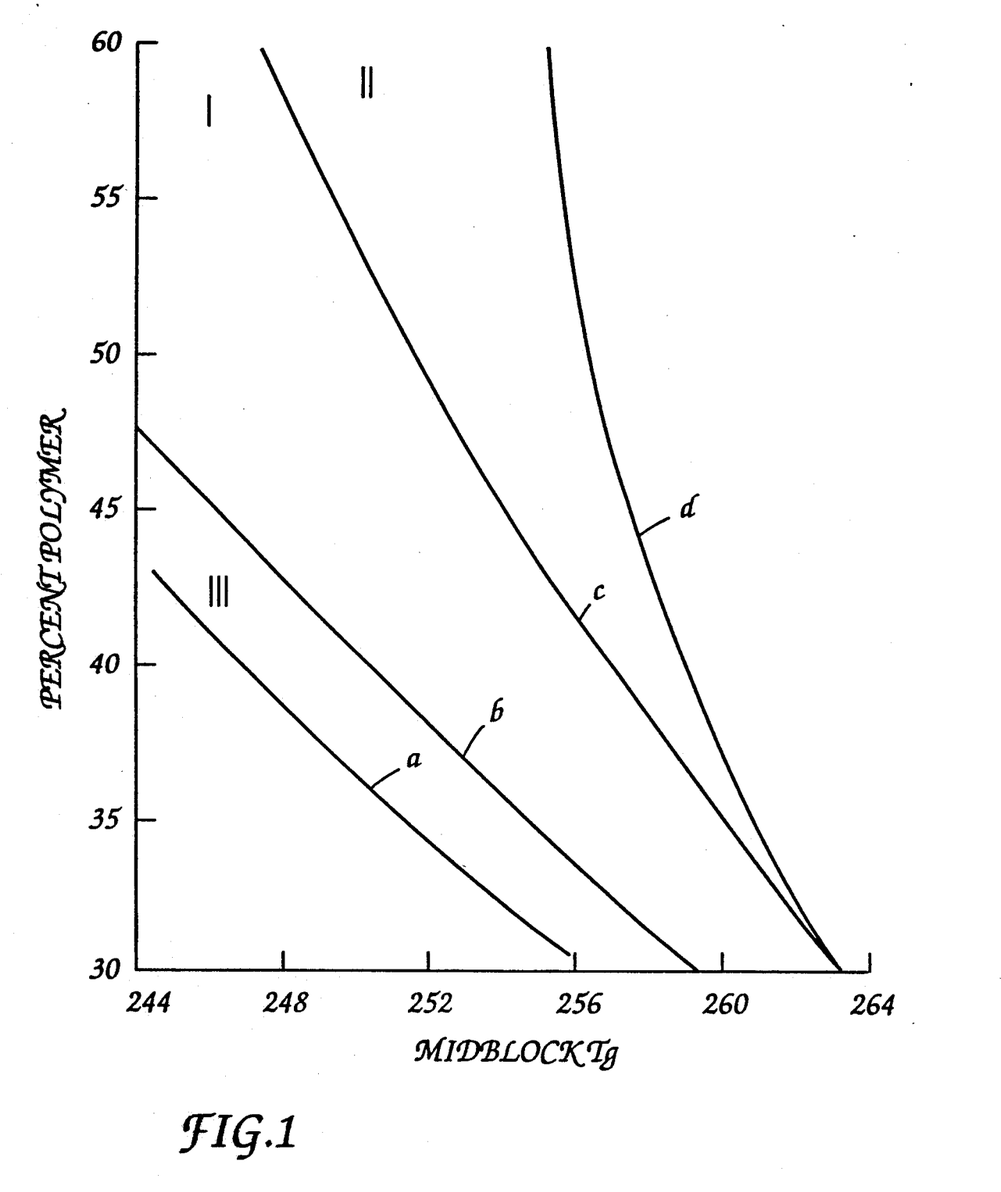
FIG. 1 is a diagram outlining the preferred adhesive compositions based on percent elastomer and CMTg.
Figure 2:
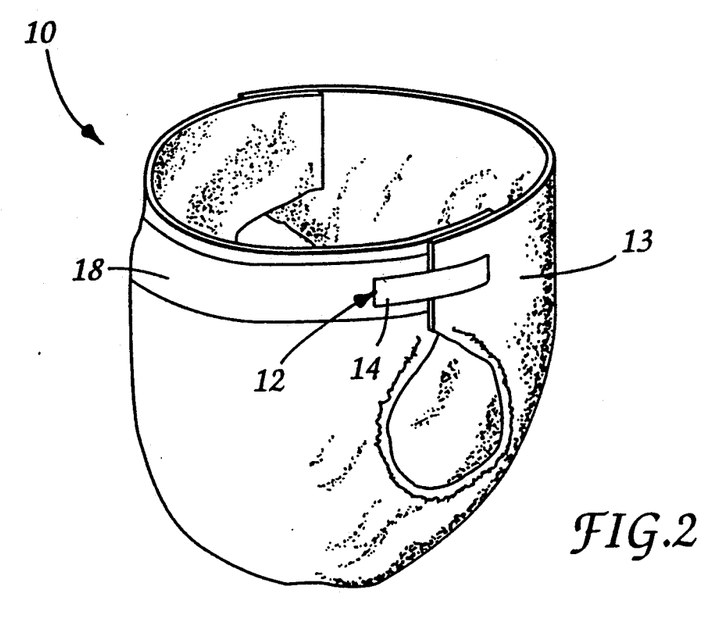
FIG. 2 is a diaper using the closure system of the invention.

The diaper closure system of the invention can be used with any conventional diaper FIG. 1 which uses an adhesive fastening tab 14 to effect closure of the baby diaper or adult incontinence device 10, by attachment to a Low Adhesion Backsize (LAB) treated polyolefin or like film 18. The film 18 is generally a reinforcing film, typically attached to a liquid impermeable outer shell 13 11 of the diaper. Many diapers are provided with a reinforced area where the tape adheres to the diaper. These reinforcing areas are generally formed of a relatively stiff polymer film, such as a polypropylene film, which is generally attached directly to a liquid impermeable outer shell film. These reinforcing films are typically supplied as a tape in a roll form with the adhesive preapplied. In order to unroll the tape from the roll the tapes are provided with what is termed a low adhesion backsize (LAB) by chemical or like treatment. A typical LAB treatment is a urethane coating. However, reinforcing film cut from these LAB-treated tapes complicates adhesive diaper closure systems by interfering with subsequent adhesion of the fastening tab, making the selection of the appropriate adhesive to use on the fastening tab difficult.

Two important aspects of fastening tab performance in a diaper, or the like, adhesive closure system are the shear resistance and peel strength and performance. Peel strength is important in terms of adhesive fastening tape performance and customer perception of performance. A low peel strength bond increases the risk of popping open when subjected to the forces encountered during use. Further, low peel strengths are often associated with shocky peels (generally tested at a peel rate of 12 inches per minute). Shocky peels are well understood in the art and are when the tape peels in a jerky and noisy (sounding somewhat like a zipper) manner. The adhesive fastening tab of this invention exhibits consistently high peel values to LAB treated substrates, e.g., at least about 300 grams per inch to a common urethane LAB treated polyolefin film, preferably a peel of at least 350 g/in. Further, the invention adhesive fastening tape with its high elastomeric diblock component has consistently exhibited non-shocky peels to these LAB treated polyolefin films. These consistent, substantially non-shocky peels are extremely advantageous in an adhesive closure system. Peel forces much in excess of 750 grams per inch can be perceived as too high by some end users (this depends somewhat on the user). The high peels obtainable with the invention adhesive tapes occasionally exceed 750 grams per inch, however, not excessively such as to be perceived as a problem. Overall, the high substantially non-shocky peels are advantageous to a tape closure system as described.

The shear force resistance for a commercial adhesive fastening tab is preferably at least 200 minutes and more preferably at least 300 minutes with a 1 kilogram weight. Shear resistances of less than 300 down to about 100 are still nominally functional yet are not commercially desirable. Shear values much greater than 500 contribute little added functional or commercial benefit to a diaper fastening tab.

The preferred adhesive coating thicknesses on the fastening tabs range from 20 to 75 microns, preferably from 25 to 50 microns. With too thin of an adhesive layer thickness, the adhesion properties will be adversely affected, whereas excess coating thicknesses can be wasteful.

The block copolymers employed in adhesive compositions for the invention fastening tabs are thermoplastic block copolymers having a linear configuration and having the A blocks and B blocks formed in what are termed A-B-A block copolymers and A-B block copolymers. The A-B-A block copolymer comprises 75 percent or less of the elastomer component, preferably from 35 to 70 percent; the A-B block copolymer comprises at least about 25 percent of the elastomer component, preferably from 30 to 65 percent; the A block is a monoalkenyl arene, mainly polystyrene, having a molecular weight between 4,000 and 50,000, preferably between 7,000 and 30,000. The A block content is from about 10 to 50 percent, more preferably between 10 and 30 percent. Other suitable A blocks may be formed from alphamethyl styrene, t-butyl styrene and other ring alkylated styrenes as well as mixtures thereof. B is an elastomeric conjugated diene, namely isoprene, having an average molecular weight of from about 5,000 to about 500,000, preferably from about 50,000 to 200,000. Although preferably A-B-A and A-B block copolymers will comprise the majority of the elastomer of the adhesive, other conventional diene elastomers may be used to a minor extent, such as natural rubber; butadiene, isoprene or butadiene-styrene rubber; butadiene-acrylonitrile; butyl rubber or block copolymers of these diene elastomers. The block copolymer is used in an amount ranging from about 30 to 60 weight percent, preferably at least 35 weight percent of the adhesive composition.

The tackifying resin component generally comprises a blend of a solid tackifying resin and a liquid tackifying resin, a single solid or liquid tackifying resin, or a blend of a solid tackifying resin and a liquid plasticizer and/or liquid tackifying resin. The tackifying resins can be selected from the group of resins at least partially compatible with the B blocks of the elastomeric materials of this invention. Such tackifying resins include those aliphatic hydrocarbon resins made from the polymerization of a feed stream consisting mainly of unsaturated species containing four to six carbon atoms; rosin esters and rosin acids; mixed aliphatic/aromatic tackifying resins; polyterpene tackifiers; and hydrogenated tackifying resins. The hydrogenated resins can include resins made from the polymerization and subsequent hydrogenation of a feedstock consisting mostly of dicyclopentadiene; resins produced from the polymerization and subsequent hydrogenation of pure aromatic feedstocks such as styrene, alphamethylstyrene, vinyl toluene; resins fashioned from the polymerization and subsequent hydrogenation of an unsaturated aromatic feedstream wherein the feedstream mainly contains species having from 7 to 10 carbon atoms; hydrogenated polyterpene resins; and hydrogenated aliphatic and aliphatic-/aromatic resins. Preferred tackifying resins include the aliphatic hydrocarbon resins and the hydrogenated resins. Especially preferred are the aliphatic hydrocarbon resins.

The liquid plasticizers suitable for use in the adhesive compositions of this invention include naphthenic oils, paraffinic oils, aromatic oils, and mineral oils. Preferred plasticizing liquids include naphthenic oils and slightly aromatic oils.

The adhesive preferably is tackified with a solid tackifying resin with a liquid plasticizer or liquid resin of the above described preferred types.

Preferably, the solid tackifying resin used is one that is compatible with the elastomeric conjugated diene block and is preferably a tackifying resin having a softening point between 80° and 115° C., such as is produced from polymerization of a stream of aliphatic petroleum derivatives of dienes and monoolefins having 4 to 9 carbon atoms as is disclosed in U.S. Pat. Nos. 3,932,328 and 3,954,692, the substance of which are incorporated herein by reference. Particularly preferred are tackifying resins resulting from the copolymerization of a feed comprised predominately of $C_5$ carbon atom species such as piperylene and 2-methyl-2-butene or isoprene, commercially available, for example, as Wingtack TM 95 and Wingtack TM Plus, respectively, from Goodyear Chemical Co.

The adhesive compositions can also be modified with well known additives such as pigments, fillers, stabilizers and antioxidants for their conventional purposes.

The fastening tab is formed by placing the adhesive described above on a conventional substrate. The fastening tab substrate can suitably be formed of a synthetic polymer such as polyolefins (e.g., polypropylene), polyesters, polyamides or the like. Natural backings such as Kraft paper backings may also be used. The adhesive can be applied by any conventional method including melt coating, gravure, coextrusion, solvent coating and the like.

The CMTg can be calculated using the Fox Equation from measuring the Tg of the midblock of the elastomeric block copolymer and the measured Tg of each tackifying resin and liquid plasticizer oil. The Tg for each component is measured using a differential scanning calorimeter such as a DSC-7, manufactured by Perkin-Elmer. The Tg is measured on the second heating run using a scan rate of 20 degrees Centigrade per minute. The first heating run is made up to well above the softening point of the test material. The sample is subsequently quenched to well below the Tg of the material. Antioxidants added to the adhesive are not figured into the calculation of the CMTg. The Fox Equation is:

$$\frac{\Sigma_i W_i}{CMTg} = \Sigma_i \frac{W_i}{Tg_i}$$

where $W_i$ is the weight fraction of component i and $Tg_i$ is the glass transition temperature of component i. Only the midblock portion of the block copolymer is included in the calculation of the CMTg. For a styrene/isoprene block copolymer, the midblock is the polyisoprene portion of the molecule.

The adhesive fastening tab is used in conjunction with a release tape where the fastening end of the fastening tab is placed prior to placement on the frontal reinforcing film or tape. The release tape can be of conventional design. One side will have a pressure-sensitive adhesive coating for adhering it preferably to the nonwoven inner liner of the diaper. The opposing side will be coated with a release agent such as crosslinked poly(dimethyl-siloxane).

The fastening tab of the invention is designed for use with frontal tapes having low adhesion backsize coatings such as an urethane, as is described in U.S. Pat. No. 2,532,011 (Dahlquist et al.). These frontal tapes, as described above, serve as the attachment surfaces for the fastening tab when the diaper, or the like, is in use.

Two conventional surface textures on a frontal tape are smooth surfaces such as is obtained with a biaxially oriented polypropylene or textured surfaces as is obtained with a matte-cast film. It has been found that different ranges of the invention fastening tab adhesive compositions work with the two different surface textures. These different compositional ranges are depicted in FIG. 1.

There are three compositional spaces depicted in FIG. 1 that being I, II, and III. These spaces are bounded on the bottom by compositions with 30 percent elastomer and at the top by compositions with 60 percent elastomer. The regions I and II are bounded at the left by compositions with CMTg's of greater than 244 Kelvin. Those adhesive compositions falling within region I have been found to provide superior performance as to both types of LAB coated frontal tapes (both smooth and matte finish). Namely, region I compositions provide smooth, or substantially non-shocky, peels, high peel strengths, and good or adequate shear resistance performance with the preferred tackifiers. For smooth frontal reinforcing films, preferred region I also extends into region III. Conversely, for matte LAB-coated frontal reinforcing films, the preferred region I extends into region II. The region III compositions again show smooth and high peels to the matte film, however, do not necessarily have adequate shear resistance to standard matte surface textures.

The above described behavior depicted in FIG. 1 is altered with higher diblock content elastomers (e.g., greater than 45 percent). These higher diblock elastomer-based adhesives exhibit improved non-shocky peel at higher CMTg values, for a given percent elastomer. As such, the upper limit on peel performance with respect to the described LAB-coated substrates (defined by lines c and d) will shift to the right for higher elastomeric diblock-containing adhesive compositions.

An alternative embodiment of the invention is found for adhesives having a composite midblock glass transition temperature below 244 Kelvin to about 230 Kelvin. It has been found that such adhesives can provide very smooth or non-shocky peel performance, however, at a reduction in peel performance as one approaches lower CMTg values. Lines a and b in FIG. 1 rise in this region to reach apexes or begin to flatten out at about 238 and 236 Kelvin CMTg, and 60 and 70 percent polymer, respectively, then continue to flatten until about 230 Kelvin, at which point peel performance generally becomes unacceptable. In this lower CMTg region, the shear performance is lower except at high polymer levels, as region III between lines a and b widens. The lowering of shear performance is also noted against polyethylene film. However, this is advantageous as these tapes are less likely to tear a thin polyethylene backsheet if accidentally adhered to the backsheet. However, for adhesives in this region, it has been found useful to use a separate adhesive layer on the end of the fastening tab 14 permanently attached to the diaper. Functional adhesives are obtainable with a polymer weight percent of from about 45 to 95 percent, preferably 45 to 80 percent.

The CMTg values described above, although an excellent predictor of peel behavior for a given percent diblock adhesive composition, may not adequately predict shear performance with respect to certain non-preferred tackifiers and tackifying systems or release coatings. For these systems, shear can be raised within the teachings of this invention by increasing the elastomer and/or solid resin content of the adhesive composition used within the outlined CMTg ranges.

A further aspect of the adhesive formulation used is, it is generally suited to hot-melt coating techniques, which is advantageous in terms of environmental impact.

The following examples are the currently contemplated preferred modes for carrying out the invention and should not be considered as limiting thereof unless otherwise indicated.

EXAMPLES 1-35

The samples were prepared by coating the adhesives as listed in Table 1 onto cast polypropylene films, exhibiting a matte finish. For the examples, the polypropylene film was 4 mils(100 microns) thick and the adhesives were applied from a 50% solids solution in toluene and heptane (4 to 1 blend) in a conventional fashion. In all examples and counterexamples, the thickness of the adhesive is around 12 grains/24 in$^2$ (50 microns). For each adhesive, 1% by weight of Irganox TM 1010, a hindered phenol antioxidant available from Ciba-Geigy, was added.

The resulting adhesives had the following compositions (the values in parentheses in Table 1 represent the percent of that particular component in the adhesive composition).

TABLE 1

| Ex. | CMTq | Elastomer(s) | Diblock Percent | Liquid Resin/Oil | Solid Resin |
|---|---|---|---|---|---|
| 1 | 254 | Kraton TM 1112 (52) | 40 | Shellflex TM 371 (2.9) | Wingtack Plus TM (45.1) |
| 2 | 245 | Kraton TM 1112 (52) | 40 | Shellflex TM 371 (11.2) | Wingtack Plus TM (36.8) |
| 3 | 264 | Kraton TM 1112 (30) | 40 | Shellflex TM 371 (12.8) | Wingtack Plus TM (57.2) |
| 4 | 261 | Kraton TM 1112 (35) | 40 | Shellflex TM 371 (11.2) | Wingtack Plus TM (53.8) |
| 5 | 259 | Kraton TM 1112 (39) | 40 | Shellflex TM 371 (9.5) | Wingtack Plus TM (51.5) |
| 6 | 256 | Kraton TM 1112 (43) | 40 | Shellflex TM 371 (8.8) | Wingtack Plus TM (48.2) |
| 7 | 252 | Kraton TM 1112 (47) | 40 | Shellflex TM 371 (9.0) | Wingtack Plus TM (44.0) |
| 8 | 247 | Kraton TM 1112 (56) | 40 | Shellflex TM 371 (5.9) | Wingtack Plus TM (38.1) |
| 9 | 244 | Kraton TM 1112 (60) | 40 | Shellflex TM 371 (5.2) | Wingtack Plus TM (34.8) |
| 10 | 247 | Kraton TM 1112 (38) | 40 | Shellflex TM 371 (21.4) | Wingtack Plus TM (40.6) |
| 11 | 246 | Kraton TM 1112 (45) | 40 | Shellflex TM 371 (16.3) | Wingtack Plus TM (38.7) |
| 12 | 250 | Kraton TM 1112 (42) | 40 | Shellflex TM 371 (15.1) | Wingtack Plus TM (42.9) |
| 13 | 255 | Kraton TM 1112 (35) | 40 | Shellflex TM 371 (16.5) | Wingtack Plus TM (48.5) |
| 14 | 253 | Kraton TM 1111 (26) Kraton TM 1112 (26) | 27.5 | Shellflex TM 371 (4.7) | Wingtack Plus TM (43.3) |
| 15 | 244 | Kraton TM 1111 (26) Kraton TM 1112 (26) | 27.5 | Shellflex TM 371 (12.9) | Wingtack Plus TM (34.1) |
| 16 | 253 | Kraton TM 1111 (26) Shell RP6403 (26) | 35 | Shellflex TM 371 (4.7) | Wingtack Plus TM (43.3) |
| 17 | 244 | Kraton TM 1111 (26) Shell RP6403 (26) | 35 | Shellflex TM 371 (12.9) | Wingtack Plus TM (34.1) |
| 18 | 254 | Kraton TM 1112 (52) | 40 | Shellflex TM 371 (2.9) | Wingtack Plus TM (45.1) |
| 19 | 245 | Kraton TM 1112 (52) | 40 | Shellflex TM 371 (11.2) | Wingtack Plus TM (36.8) |
| 20 | 253 | Kraton TM 1112 (26) Shell RP6403 (26) | 47.5 | Shellflex TM 371 (3.8) | Wingtack Plus TM (44.2) |
| 21 | 244 | Kraton TM 1112 (26) Shell RP6403 (26) | 47.5 | Shellflex TM 371 (12.2) | Wingtack Plus TM (35.8) |
| 22 | 245 | Shell RP6403 (52) | 55 | Shellflex TM 371 (2.9) | Wingtack Plus TM (45.1) |
| 23 | 254 | Shell RP6403 (52) | 55 | Shellflex TM 371 (11.2) | Wingtack Plus TM (36.8) |
| 24 | 254 | Kraton TM 1112 (52) | 40 | Shellflex TM 371 (2.9) | Wingtack Plus TM (45.1) |
| 25 | 245 | Kraton TM 1112 (52) | 40 | Shellflex TM 371 (11.2) | Wingtack Plus TM (36.8) |
| 26 | 254 | Kraton TM 1112 (52) | 40 | Zonarez TM A-25 (5.0) | Escorez TM 1310 (43.0) |
| 27 | 245 | Kraton TM 1112 (52) | 40 | Zonarez TM A-25 (21.8) | Escorez TM 1310 (26.2) |
| 28 | 254 | Kraton TM 1112 (52) | 40 | Shellflex TM 371 (12.7) | Zonarez TM A-135 (35.3) |
| 29 | 245 | Kraton TM 1112 (52) | 40 | Shellflex TM 371 (19.2) | Zonarez TM A-135 (28.8) |
| 30 | 254 | Kraton TM 1112 (52) | 40 | ECR TM 143-H (4.0) | Arkon TM P100 (44.0) |
| 31 | 245 | Kraton TM 1112 (52) | 40 | ECR TM 143-H (19.9) | Arkon TM P100 (28.1) |

TABLE 1-continued

| Ex. | CMTq | Elastomer(s) | Diblock Percent | Liquid Resin/Oil | | Solid Resin | |
|---|---|---|---|---|---|---|---|
| 32 | 254 | Kraton TM 1112 (52) | 40 | Escorez TM 2520 | (5.1) | Escorez TM 1310 | (42.9) |
| 33 | 245 | Kraton TM 1112 (52) | 40 | Escorez TM 2520 | (22.7) | Escorez TM 1310 | (25.3) |
| 34 | 254 | Kraton TM 1112 (52) | 40 | Escorez TM 2520 | (7.6) | Regalite TM 355 | (40.4) |
| 35 | 245 | Kraton TM 1112 (52) | 40 | Escorez TM 2520 | (24.2) | Regalite TM 355 | (23.8) |
| Counter-examples | | | | | | | |
| C1 | 254 | Kraton TM 1111 (52) | 15 | Shellflex TM 371 | (4.7) | Wingtack Plus TM | (43.3) |
| C2 | 245 | Kraton TM 1111 (52) | 15 | Shellflex TM 371 | (12.7) | Wingtack Plus TM | (35.3) |
| C3 | 254 | Kraton TM 1111 (52) | 15 | Shellflex TM 371 | (4.7) | Wingtack Plus TM | (43.3) |
| C4 | 245 | Kraton TM 1111 (52) | 15 | Shellflex TM 371 | (12.7) | Wingtack Plus TM | (35.3) |
| C5 | 263 | Kraton TM 1107 (33.5) | 15 | Zonarez TM A-25 | (20.0) | Escorez TM 1310 | (46.5) |
| C6 | 263 | Kraton TM 1107 (39) | 15 | Wingtack TM 10 | (10.8) | Wingtack Plus TM | (50.2) |
| C7 | 257 | Kraton TM 1111 (40) | 15 | Shellflex TM 371 | (12.0) | Wingtack Plus TM | (48.0) |
| C8 | 255 | Kraton TM 1111 (38) | 15 | Shellflex TM 371 | (15.3) | Wingtack Plus TM | (46.7) |

Kraton TM 1107 is a polystyrene-isoprene linear block copolymer available from Shell Chemical Co. having a styrene/isoprene ratio of 14/86, approximately 15 to 20 percent diblock (A-B) and, 80 to 85 percent triblock (A-B-A) and a midblock Tg of 215 Kelvin.

Kraton TM 1111 is a polystyrene-isoprene linear block copolymer available from Shell Chemical Co. having a styrene content of about 21 percent, approximately 15 percent diblock and 85 percent triblock and a midblock Tg of 215 Kelvin.

Kraton TM 1112 is a polystyrene-isoprene linear block copolymer available from Shell Chemical Co. having a styrene content of about 14 percent, approximately 40 percent diblock and 60 percent triblock and a midblock Tg of 215 Kelvin.

Shell TM RP6403 is a polystyrene-isoprene linear block copolymer available from Shell Chemical Co. having a styrene content of about 14 percent, approximately 55 percent diblock and 45 percent triblock and a midblock Tg of 215 Kelvin.

Escorez TM 1310 is a solid $C_5$ tackifying resin available from Exxon Chemical Corp. having a Tg of 313.5 Kelvin.

Wingtack TM Plus is a solid $C_5$ tackifying resin with a Tg of 315 Kelvin available from Goodyear Chemical Co.

Wingtack TM 10 is a liquid $C_5$ hydrocarbon resin with a Tg of 245 Kelvin also from Goodyear Chemical Co.

Zonarez TM A-25 is a liquid alpha pinene tackifying resin with a Tg of 251 Kelvin available from Arizona Chemical Co.

Zonarez TM A-135 is a solid alpha pinene resin with a Tg of 367 Kelvin from Arizona Chemical Co.

Shellflex TM 371 is a naphthenic oil having about 10% aromatics measured by clay-gel analysis having a Tg of 209 Kelvin and is available from Shell Chemical Co.

ECR TM 143H is a hydrogenated aliphatic hydrocarbon resin with a Tg of 247 Kelvin available from Exxon Chemical Corp.

Escorez TM 2520 is a hydrogenated aliphatic hydrocarbon resin with a Tg of 253 Kelvin available from Exxon Chemical Corp.

Arkon TM P100 is a hydrogenated $C_9$ tackifying resin with a Tg of 312.5 Kelvin available from Arakawa Chemical Co.

Regalite TM 355 is a hydrogenated rosin acid with a Tg of 318.1 Kelvin available from Hercules Inc.

The examples were then tested for their shear and 135° peel to a smooth frontal tape surface of biaxially oriented polypropylene (BOPP), and a matte finish cast polypropylene frontal tape, both having an LAB coating. The LAB was a copolymer of vinyl acetate and vinyl alcohol where some of the alcohol groups in the polymer backbone have been reacted with octadecyl isocyanate. The results are depicted in Table II.

TABLE 2

| Ex. | BOPP Shear | BOPP Peel | Shocky | Matte Shear | Matte Peel | Shocky |
|---|---|---|---|---|---|---|
| 1 | 1400 | 287 | Yes | 1400 | 874 | No |
| 2 | 1400 | 461 | No | 220 | 586 | No |
| 3 | 450 | 213 | Yes | 120 | 662 | Yes |
| 4 | 1150 | 292 | Yes | 220 | 750 | S |
| 5 | 1400 | 342 | Yes | 700 | 714 | S |
| 6 | 1400 | 341 | Yes | 1210 | 656 | No |
| 7 | 1400 | 497 | S | 1040 | 540 | No |
| 8 | 1400 | 425 | No | 1400 | 464 | NO |
| 9 | 1400 | 416 | No | 1100 | 390 | No |
| 10 | 40 | 285 | No | 10 | 457 | No |
| 11 | 500 | 471 | No | 76 | 534 | No |
| 12 | 570 | 569 | No | 140 | 619 | No |
| 13 | 240 | 629 | No | 105 | 693 | No |
| 14 | 1400 | 238 | Yes | 1400 | 846 | No |
| 15 | 1150 | 426 | No | 220 | 445 | No |
| 16 | 1400 | 291 | S | 1400 | 920 | No |
| 17 | 990 | 450 | No | 350 | 509 | No |
| 18 | 1400 | 287 | Yes | 1400 | 874 | No |
| 19 | 1400 | 461 | No | 220 | 586 | No |
| 20 | 1400 | 529 | No | 1400 | 761 | No |
| 21 | 430 | 401 | No | 210 | 620 | No |
| 22 | 405 | 525 | No | 300 | 665 | No |
| 23 | 1400 | 380 | No | 1400 | 847 | No |
| 24 | 1400 | 287 | Yes | 1400 | 874 | No |
| 25 | 1400 | 461 | No | 220 | 586 | No |
| 26 | 1400 | 235 | Yes | 1400 | 825 | No |
| 27 | 370 | 415 | No | 100 | 552 | No |
| 28 | 1400 | 261 | Yes | 1400 | 699 | No |
| 29 | 80 | 463 | No | 16 | 372 | No |
| 30 | 1400 | 281 | Yes | 1400 | 828 | No |
| 31 | 810 | 467 | No | 400 | 548 | No |
| 32 | 1400 | 362 | S | 1400 | 814 | No |
| 33 | 260 | 402 | No | 30 | 541 | No |
| 34 | 1400 | 370 | S | 1400 | 476 | No |
| 35 | 405 | 460 | No | 40 | 268 | No |
| C1 | 1400 | 193 | Yes | 1400 | 872 | Yes |
| C2 | 1400 | 448 | S | 210 | 469 | Yes |
| C3 | 1400 | 168 | Yes | 1400 | 801 | Yes |
| C4 | 1400 | 468 | S | 390 | 443 | Yes |
| C5 | 1400 | 145 | Yes | 740 | 545 | Yes |
| C6 | 700 | 179 | Yes | 500 | 630 | Yes |
| C7 | 1400 | 233 | Yes | 1400 | 769 | Yes |

TABLE 2-continued

| Ex. | BOPP Shear | BOPP Peel | Shocky | Matte Shear | Matte Peel | Shocky |
|---|---|---|---|---|---|---|
| C8 | 1400 | 432 | S | 60 | 502 | Yes |

S = Semi-shocky

Examples 1-13 demonstrate the effect of CMTg on the performance characteristics of the diaper adhesive fastening tapes. The results of this CMTg variation is depicted graphically in FIG. 1. Line a in FIG. 1 delineates acceptable from unacceptable shear performance to the smooth BOPP film. Below line a, the shear was found to be unacceptable. Below line b, similarly unacceptable shear performance to the cast matte film was encountered. Line c delineates acceptable from unacceptable peel performance. With respect to the smooth BOPP film above line c, the tapes exhibited shocky peels, whereas below line c, the tapes all exhibited smooth or semi-shocky peels. Similarly, line d delineates acceptable versus unacceptable performance with respect to the cast matte film. Thus, overall acceptable performance is between lines a and c for smooth BOPP and between lines b and d for matte cast film for this resin system.

Examples 14 to 23 are examples of the effect of variance of the diblock content of the elastomeric component within the broad preferred range. No significant effects are noticed with the above defined preferred areas I to III when the diblock percentage is varied with the noted exception of examples 20 and 23 which perform better than comparable examples with respect to their peel performance on the smooth BOPP film. This indicates that for higher diblock content adhesives region II provides acceptable performance. Examples 18 and 19 are identical to examples 1 and 2.

Examples 24 to 35 show the effect of varying the tackifying system from the preferred compounding oil and $C_5$ solid tackifier.

Examples 26 and 27 use a liquid alpha pinene resin instead of the oil. This creates a slight decrease in shear and peel performance (more-so shear) which is more noticeable at the lower CMTg formulation (more of the liquid alpha pinene resin).

Examples 28 and 29 use a solid alpha pinene. In this case the more noticeable performance degradation is at the lower CMTg formulation where unacceptable shear is encountered despite these formulations falling within region I.

Examples 26-29 appear to indicate that non-preferred alpha pinene and like higher aromatic tackifiers can be used, but possibly only in a blend with more solid tackifiers at lower CMTg values within the preferred range.

Examples 30 and 31 use a liquid aliphatic tackifying resin and a solid hydrogenated $C_9$ tackifying resin. There is no significant performance variation with these particular tackifiers as compared to Examples 24 and 25.

Examples 32 and 33 use a liquid hydrogenated hydrocarbon resin compared to examples 24 and 25. These examples exhibit better peel to smooth film at higher CMTg values within the preferred regions yet unacceptable shear values to cast matte film within the preferred region (region I). This indicates a shift in the useful CMTg values for this particular type of resin.

Examples 34 and 35 also use a hydrogenated rosin acid, however, with no significant additional effects (compared to examples 32 and 33).

COUNTEREXAMPLES

Counterexamples 1 to 8 demonstrate the effect of lowering the diblock content of the elastomer component. The CMTg values for counterexamples 1 and 3 and 2 and 4 are substantially identical (the variations in properties are minor due to experimental error in measurements or lot variations in the raw materials) and are within the preferred CMTg ranges (254 and 245), yet the peel values are shocky or semi-shocky as compared to otherwise compositionally identical, e.g., examples 1 and 2, which provide non-shocky peels. This demonstrates the effectiveness of high diblock content in reducing shocky peels, while still providing elastomeric compositions with adequate shear performance.

EXAMPLES 36-49

These examples were prepared, as with Examples 1-35, from a solution coated onto a polypropylene film. The adhesive thickness was about 12 grains/24 in² (about 50 microns). The resulting adhesives had the compositions set forth in Table 3 below in percent by weight.

TABLE 3

| EXAMPLE | CMTg | ELASTOMER[1] | LIQUID RESIN | SOLID RESIN |
|---|---|---|---|---|
| 36 | 241 | 42 | 49.2[2] | 8.8[4] |
| 37 | 241 | 53 | 29.1[2] | 17.9[4] |
| 38 | 241 | 58 | 20.0[2] | 22.0[4] |
| 39 | 241 | 67 | 3.6[2] | 29.4[4] |
| 40 | 235 | 58 | 32.8[2] | 9.2[4] |
| 41 | 235 | 67 | 16.2[2] | 16.8[4] |
| 42 | 230 | 67 | 27.2[2] | 5.8[4] |
| 43 | 241 | 53 | 25.6[3] | 21.4[5] |
| 44 | 241 | 58 | 17.5[3] | 24.5[5] |
| 45 | 241 | 67 | 2.9[3] | 30.1[5] |
| 46 | 235 | 43 | 53.6[3] | 3.4[5] |
| 47 | 235 | 53 | 37.2[3] | 9.8[5] |
| 48 | 235 | 67 | 14.2[3] | 18.8[5] |
| 49 | 230 | 67 | 28.1[3] | 4.9[5] |

[1] Kraton TM 1112
[2] Escorez TM 2520
[3] ECR TM 143H
[4] Escorez TM 1310
[5] Arkon TM P-100

These tapes were then tested for 135° peel and shear performance to the same BOPP and cast polyproplene films as Examples 1-35. The results are depicted in Table 4. All the peels were non-shocky.

TABLE 4

| EXAMPLE | BOPP SHEAR | BOPP PEEL | MATTE SHEAR | MATTE PEEL |
|---|---|---|---|---|
| 36 | 10 | 147 | 10 | 198 |
| 37 | 96 | 323 | 11 | 200 |
| 38 | 224 | 330 | 29 | 260 |
| 39 | 1400 | 349 | 1400 | 338 |
| 40 | 26 | 259 | 10 | 158 |
| 41 | 386 | 258 | 61 | 196 |
| 42 | 111 | 147 | 10 | 49 |
| 43 | 213 | 279 | 20 | 230 |
| 44 | 471 | 342 | 129 | 220 |
| 45 | 1400 | 228 | 1400 | 170 |
| 46 | 11 | 216 | 10 | 170 |
| 47 | 61 | 279 | 10 | 172 |
| 48 | 316 | 207 | 23 | 145 |
| 49 | 68 | 92 | 10 | 26 |

In this lower CMTg range, the peel performance to the BOPP and cast matte films was lower than for Examples 1-35, which has higher CMTg values. However, the peel performance was still functional and non-shocky.

Below a CMTg of 244, a line a rises, then reaches an apex at about 238 Kelvin and 60 percent polymer, than flattens, with substantially all tack lost at CMTg values below 230 Kelvin. Similarly, line b rises and reaches an apex at about 236 Kelvin and 70 percent polymer. Lines c and d are not applicable below an adhesive CMTg of 244 Kelvin.

EXAMPLES 50-56

These tapes were hot-melt coated onto a backing a coating weight of about 12 grains/24 in$^2$ (50 microns). The adhesive formulations are given below in Table 5 in percent by weight.

TABLE 5

| EXAMPLE | CMTg | ESLAS-TOMER[1] | PLASTICIZER[2] | SOLID RESIN[3] |
|---|---|---|---|---|
| 50 | 244 | 47 | 17.8 | 35.2 |
| 51 | 244 | 50 | 15.3 | 34.7 |
| 52 | 244 | 53 | 12.8 | 34.2 |
| 53 | 244 | 56 | 10.3 | 33.7 |
| 54 | 241 | 50 | 18.1 | 31.9 |
| 55 | 241 | 53 | 15.6 | 31.4 |
| 56 | 241 | 56 | 13.0 | 31.0 |

[1] RP 6411- a polyisoprene-polystyrene block copolymer with a midblock Tg of about 215 Kelvin, approximately 65 percent diblock and 35 percent triblock, available from Shell Chemical Co.
[2] Shellflex ™ 371
[3] Wingtack ™ Plus These tapes were then tested for 135° peel and shear performance, as per the previous examples, except that the tapes were tested against a standard embossed diaper polyethylene film instead of the matte cast polypropylene. The results are given in Table 6 below.

TABLE 6

| EXAMPLE | SHEAR BOPP | BOPP PEEL | POLY SHEAR | POLY PEEL |
|---|---|---|---|---|
| 50 | 211 | 602 | 59 | 638 |
| 51 | 266 | 630 | 70 | 724 |
| 52 | 573 | 685 | 332 | 775 |
| 53 | 1176 | 633 | 794 | 852 |
| 54 | 263 | 575 | 63 | 578 |
| 55 | 263 | 624 | 59 | 670 |
| 56 | 388 | 630 | 108 | 668 |

All the tapes exhibited substantially non-shocky peel performance (however, Example 54 was slightly shocky against the BOPP film). Lines a and b shifted down somewhat for these higher diblock adhesives at CMTg values less than 244 Kelvin and, surprisingly, the peel performance to the BOPP film was superior to the lower diblock adhesive of Examples 36-49. However, a problem with these adhesives, particularly at the lower polymer levels, e.g., less than about 50 percent at 244 Kelvin and less than about 60 percent at 241 Kelvin and below, is that the adhesives exhibit poor shear adherence to diaper polyethylene. Generally, this would correspond to adhesives close to and to the left of line b in the region above 244 Kelvin CMTg in FIG. 1 (and the described extension of this line in the region below 244 Kelvin CMTg). With these adhesives, only the free end of the fastening tab is coated with these adhesives, the end of the diaper fastening tab permanently adhered to the diaper polyethylene (generally termed the manufacturer's bond) is coated with a separate adhesive showing good adherence to polyethylene. Generally, the adhesives falling to the right of line b, and preferably to the right of line c, show good shear performance to diaper polyethylene, however, adhesion to polyethylene does noticeably drop at CMTg values much in excess of 275 Kelvin. The adhesive of Examples 50-56 could then be used on the free end of the diaper fastening tab to adhere to the BOPP reinforcing tape to effect closure of the diaper.

Test Methods

135 Degree Peel from Frontal Tape

The peel adhesion test is a 135 degree peel from a smooth frontal tape surface of biaxially oriented polypropylene(BOPP) or a matte cast polypropylene, having a LAB on it. The peel rate is 12 inches per minute. The tape samples are rolled down onto the frontal tape substrate using two passes of a 4.5 pound roller. This test is a variation on PSTC-5. The data is reported in grams per inch and was run at 70° F. and 50 percent relative humidity.

Shear from Frontal Tape Substrate

The shear adhesion is measured by determining the length of time it takes for a 1 inch by 1 inch sample to shear off a frontal tape substrate under a 1 kilogram load. The frontal tape is either a smooth frontal tape(BOPP) with a LAB as described above or a matte polypropylene(PP) with an LAB. The 21" by 61" piece of frontal tape is laminated to a 21" by 61" piece of reinforcing tape (DPDY-9377) in order to enhance the stiffness of the substrate. On the side opposite the reinforcing tape, a one by two inch area of the test tape is rolled down onto the frontal tape using 2 passes of a 4.5 pound roller. The overlap area between the test tape and the substrate is one by one inch. The laminated substrate and the test tape are hung vertically in a 400° C. oven for 15 minutes after which a 1 kilogram weight is hung from the test tape, generating a shear load at a 180° angle. The time in minutes for the weight to drop is used as the measure of the shear adhesion.

Other embodiments of the invention will be apparent to those skilled in the art from the consideration of the specification of or practice of the invention disclosed herein. It is intended that the specifications and examples be considered as exemplary, with the true scope and spirit of the invention being indicated by the following claims.

We claim:

1. A diaper tape closure system comprising a disposable diaper having a first closure surface comprising a reinforcement film substrate, the reinforcement film substrate having a first inner face having an adhesive layer and a second outer face having a low adhesion backsize (LAB) layer, a second closure surface comprising a fastening tab having a backing substrate and an adhesive layer on said backing substrate, for removable attachment to said first closure surface LAB layer second outer face, said fastening tab adhesive layer consisting essentially of:
   (a) 30 to 60 weight percent of an elastomer component comprised of a block copolymer with A blocks derived primarily from styrene and B blocks derived primarily from isoprene wherein at least 25 percent of the block copolymer is in the form of an AB diblock copolymer,
   (b) 40 to 70 weight percent of a solid B block compatible tackifying resin admixed when necessary with a liquid tackifying resin or a processing oil so as to provide an adhesive composition having a CMTg of from 244 to 265 Kelvin which adhesive layer on said fastening tape exhibits a shear adhesion of at least about 200 minutes to the first closure surface LAB layer second outer face and substantially non-shocky peel at 135 degrees of at least about 300 grams per inch tested against a LAB coated BOPP film and wherein the tape adhesive composition falls within one of regions I to III of FIG. 1, wherein the diaper is closed by attaching said fastening tab to said first closure surface LAB layer second outer face.

2. The tape closure of claim 1 wherein the elastomer component further comprises an A-B-A triblock copolymer.

3. The tape closure system of claim 1 wherein the reinforcement film substrate has a smooth surface on the LAB layer face.

4. The tape closure system of claim 1 wherein the LAB reinforcement film substrate has a matte surface on the LAB layer face.

5. The tape closure system of claim 1 wherein the reinforcement film substrate is a polyolefin film diaper frontal tape.

6. The tape closure system of claim 3 wherein the LAB Layer is a urethane coating.

7. The tape closure system of claim 4 wherein the LAB layer is a urethane coating.

8. The tape closure system of claim 1 wherein the 135 degree peel of the fastening tape from the first closure surface reinforcement film substrate LAB layer second outer face is at least about 350 grams per inch.

9. A diaper tape closure system comprising a disposable diaper having a first closure surface comprising a reinforcement film substrate, the reinforcement film substrate having a first inner face having an adhesive layer and a second outer face having a low adhesion backsize (LAB) layer, a second closure surface comprising a fastening tab having a backing substrate and an adhesive layer on said backing substrate, for removable attachment to said first closure surface LAB layer second outer face, said fastening tab adhesive layer consisting essentially of:
 (a) 45 to 95 weight percent of an elastomer component comprised of a block copolymer with A blocks derived primarily from styrene and B blocks derived primarily from isoprene wherein at least 25 percent of the block copolymer is in the form of an AB diblock copolymer,
 (b) 5 to 55 weight percent of a solid B block compatible tackifying resin admixed when necessary with a liquid tackifying resin or a processing oil so as to provide an adhesive composition having a CMTg of from 230 to 244 Kelvin which adhesive layer on said fastening tape exhibits a shear adhesion of at least about 100 minutes to the first closure surface LAB layer second outer face and substantially non-shocky peel at 135 degrees of at least about 200 grams per inch tested against a LAB coated BOPP film wherein the diaper is closed by attaching said fastening tab adhesive layer to said first closure surface LAB layer second outer face.

10. The tape closure of claim 9 wherein the elastomer component further comprises an A-B-A block copolymer.

11. The tape closure system of claim 9 wherein the tape exhibits a peel at 135 degrees of at least about 250 grams per inch.

12. The tape closure system of claim 9 wherein the reinforcement film substrate has a smooth surface on the LAB layer face.

13. The tape closure system of claim 9 wherein the reinforcement film substrate is a polyolefin film diaper frontal tape.

14. The tape closure system of claim 12 wherein the LAB layer is a urethane coating.

15. The tape closure system of claim 9 wherein the 135 degree peel of the fastening tape from the first closure surface reinforcement film substrate LAB layer second outer face is at least about 200 grams per inch.

* * * * *

UNITED STATES PATENT AND TRADEMARK OFFICE
CERTIFICATE OF CORRECTION

PATENT NO. : 5,300,057
DATED : April 5, 1994
INVENTOR(S) : Miller et al.

It is certified that error appears in the above-indentified patent and that said Letters Patent is hereby corrected as shown below:

Column 14, line 27, delete "21" by 61"" and insert --2" by 6"--.
Column 14, line 28, delete "21" by 61"" and insert --2" by 6"--.
Column 14, line 34, delete "400°C" and insert --40°C--.

Signed and Sealed this

Sixth Day of September, 1994

Attest:

BRUCE LEHMAN

Attesting Officer

Commissioner of Patents and Trademarks